(12) United States Patent
Bhat et al.

(10) Patent No.: US 10,274,568 B2
(45) Date of Patent: Apr. 30, 2019

(54) SIMULTANEOUS MULTI-SLICE MAGNETIC RESONANCE IMAGING WITH SPIN EXCITATION USING A MULTI-BAND RADIO-FREQUENCY PULSE

(71) Applicant: Siemens Healthcare GmbH, Erlangen (DE)

(72) Inventors: Himanshu Bhat, Newton, MA (US); Pedro Miguel Itriago Leon, Caracas (VE); Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 292 days.

(21) Appl. No.: 15/093,164

(22) Filed: Apr. 7, 2016

(65) Prior Publication Data
US 2017/0293010 A1    Oct. 12, 2017

(51) Int. Cl.
*G01R 33/48* (2006.01)
*G01R 33/50* (2006.01)
*G01R 33/561* (2006.01)
*A61B 5/055* (2006.01)
*A61B 5/00* (2006.01)
*G01R 33/483* (2006.01)

(52) U.S. Cl.
CPC ........ *G01R 33/5611* (2013.01); *A61B 5/0042* (2013.01); *A61B 5/055* (2013.01); *G01R 33/4835* (2013.01); *A61B 2560/0223* (2013.01)

(58) Field of Classification Search
CPC ........ G01R 33/36; G01R 33/48; G01R 33/50; G01R 33/54; G01R 33/543; G01R 33/561; G01R 33/5602; G01R 33/5611; G01R 33/5612; G01R 33/5613; G01R 33/5616; G01R 33/5621; G01R 33/5617; G01R 33/482; G01R 33/4828; G01R 33/483; G01R 33/4835
See application file for complete search history.

(56) References Cited

U.S. PATENT DOCUMENTS

2014/0253120 A1* 9/2014 Ugurbil ............... A61B 5/055
                                                    324/309
2015/0346300 A1* 12/2015 Setsompop ........ G01R 33/4828
                                                    324/309

OTHER PUBLICATIONS

Cauley et al., "Interslice Leakage Artifact Reduction Technique for Simultaneous Multislice Acquisitions," Magnetic Resonance in Medicine, vol. 72, pp. 93-102 (2014).
(Continued)

*Primary Examiner* — Son T Le
(74) *Attorney, Agent, or Firm* — Schiff Hardin LLP

(57) ABSTRACT

In a method and apparatus for acquiring magnetic resonance (MR) raw data with a simultaneous multi-slice (SMS) data acquisition sequence, nuclear spins respectively in multiple slices of the examination subject are simultaneously excited by radiating, from a radio-frequency (RF) radiator of the MR data acquisition scanner, a multi-band (MB) RF pulse. This MB RF pulse in the SMS data acquisition sequence is generated by radiating and superimposing a number of single band (SB) RF pulses emitted from said RF radiator, each having a respectively different flip angle. Raw MR data are acquired from the multiple slices of the examination subject after the simultaneous excitation of nuclear spins in the multiple slices with said MB RF pulse.

14 Claims, 4 Drawing Sheets

(56) References Cited

OTHER PUBLICATIONS

Setsompop et al., "Improving Diffusion MRI Using Simultaneous Multi-Slice Echo Planar Imaging," NeuroImage, vol. 63, pp. 569-580 (2012).
Setsompop et al., "Blipped-Controlled Aliasing in Parallel Imaging for Simultaneous Multislice Echo Planar Imaging With Reduced g-Factor Penalty," Magnetic Resonance in Medicine, vol. 67, pp. 1210-1224 (2012).
Breuer et al., "Controlled Aliasing in Parallel Imaging Results in Higher Acceleration (CAIPIRINHA) for Multi-Slice Imaging," Magnetic Resonance in Medicine, vol. 53, pp. 684-691 (2005).
Larkman et al.,, "Use of Multicoil Arrays for Separation of Signal from Multiple Slices Simultaneously Excited," Journal of Magnetic Resonance Imaging, vol. 13, pp. 313-317 (2001).
Souza et al., "SIMA: Simultaneous Multislice Acquisition of MR Images by Hadamard-Encoded Excitation," Journal of Computer Assisted Tomography, vol. 12(6) pp. 1026-1030 (1998).

\* cited by examiner

SIMULTANEOUS MULTI-SLICE MAGNETIC RESONANCE IMAGING WITH SPIN EXCITATION USING A MULTI-BAND RADIO-FREQUENCY PULSE

BACKGROUND OF THE INVENTION

Field of the Invention

The present invention concerns magnetic resonance (MR) imaging, and in particular concerns simultaneous multi-slice (SMS) MR imaging.

Description of the Prior Art

MR imaging is a widely used imaging modality for medical diagnosis as well as for material inspection.

In a magnetic resonance apparatus, the examination object (a patient, in the case of medical magnetic resonance imaging) is exposed to a strong and constant basic magnetic field, by the operation of a basic field magnet of an MR scanner, in which the examination object is situated. The MR scanner also has a gradient coil arrangement that is operated in order to activate gradient fields that spatially encode the magnetic resonance signals. The magnetic resonance signals are produced by the radiation of radio-frequency (RF) pulses from an RF radiator, such as one or more antennas, in the MR scanner. These RF pulses excite nuclear spins in the examination object, and are therefore often called excitation pulses. The excitation of the nuclear spins at an appropriate frequency gives the excited spins a magnetization that causes the nuclear spins to deviate, by an amount called the flip angle, from the alignment of the nuclear spins that was produced by the basic magnetic field. As the nuclear spins relax, while returning to alignment in the basic magnetic field, they emit MR signals (which are also RF signals), which are received by suitable RF reception antennas in the MR scanner, which may be the same or different from the RF radiator used to emit the excitation pulse.

The emitted MR signals have a signal intensity that is dependent on the exponential decay over time of the magnetization of the nuclear spins. The acquired signals are digitized so as to form raw data, which are entered into a memory that is organized as k-space, as k-space data. Many techniques are known for reconstructing an image of the examination object from the k-space data.

By appropriately selecting different characteristics of the MR data acquisition sequence that is used, the acquired signals can be differently weighted so that different sources of the detected MR signals (i.e., different tissues in the case of medical MR imaging) appear with different contrasts in the reconstructed image. In the case of medical MR imaging, a weighting is selected that causes the tissue that is important for making the intended medical diagnosis to have the best contrast (brightness) in the reconstructed image. One such type of weighting is known as T1-weighting, because it depends on the so-called T1 relaxation time of the nuclear spins.

Many different techniques are known for acquiring the raw MR data. One such technique is known as simultaneous multi-slice (SMS) acquisition, which is a technique for accelerating the acquisition of the data from a given volume of the examination object, wherein nuclear spins in multiple slices are excited simultaneously, and the resulting MR signals are simultaneously acquired from each slice. This results in a dataset in k-space that is composed of data from the multiple slices collapsed on top of each other. Techniques are known for separating or uncollapsing the data for these respective slices during image reconstruction, such as the slice GRAPPA (Generalized Autocalibration Partially Parallel Acquisitions) technique, which is schematically illustrated in FIG. 1. In the example shown in FIG. 1, multiple slices S1, S2 and S3 are excited simultaneously, resulting in each slice generating an echo train of magnetic resonance signals, which are acquired according to the known blipped CAIPIRINHA (Controlled Aliasing in Parallel Imaging Results in Higher Acceleration) technique.

Excitation of the nuclear spins in the simultaneously acquired slices is implemented with a multi-band (MB) RF pulse. An MB RF pulse is generated by the superimposition of a number of individual single band (SB) RF pulses, of the type that are typically used to excite nuclear spins in a single selected slice in conventional magnetic resonance imaging.

As noted above, the received or detected signals that result from the excitation of the nuclear spins can be given a weighting so that the signal intensity is dependent on the T1 relaxation time of the excited nuclear spins. T1 mapping (which differs from the reconstruction of a T1-weighted image) is the quantifying of the T1 relaxation time of the tissue from which the signals originate by, pixel-by-pixel in a 2D image, or voxel-by-voxel in a 3D image, analysis of the signal intensities in the reconstructed MR image. The result of this analysis is a representation of the spatial distribution of the per pixel, or per voxel, T1 values, i.e., a T1 map. T1 mapping using a multi-flip angle gradient echo sequence (i.e., a conventional single slice sequence) is implemented in commercially available magnetic resonance systems from Siemens Healthcare. This sequence requires several scans to be executed, respectively with different flip angles. A voxel-by-voxel fit of the respective images is then performed, in order to calculate a T1 map.

Conceptually, SMS might be considered as a possible technique for accelerating the acquisition of raw MR data for generating such T1 maps. Simply applying SMS acceleration to the generation of T1 maps, however, presents problems that must be taken into account and overcome, in order to make SMS acceleration meaningful in clinical practice for acquiring raw data for the subsequent generation (calculation) of T1 maps.

As shown in FIG. 2, in a conventional SMS sequence, the MB RF pulse that is radiated in an SMS sequence is formed by the simultaneous emission and superimposition of a number of SB RF pulses, that all have the same flip angle. (Although these respective pulses may have different phase curves, as shown in FIG. 2, the respective phases of the SB RF pulses, and the resulting MB RF pulse, are not relevant to the discussion herein.)

Simply applying a conventional SMS sequence in a multi-flip angle T1 mapping protocol would mean executing multiple scans with progressively increasing flip angles. For example, for acquiring data from two slices, an SMS acceleration factor of two, and two flip angles, namely Flip1 and Flip2, with Flip2>Flip1, the following two scans would have to be executed:

Scan1 using MBPulse1=SBPulse_Slice1_Flip1+
SBPulse_Slice2_Flip1

Scan2 using MBPulse2=SBPulse_Slice1_Flip2+
SBPulse_Slice2_Flip2

In this case, Scan2 (using MBPulse2) has a higher RF energy compared to Scan1 (using MBPulse 1), and may produce problems if the specific absorption rate (SAR) limit for the patient is exceeded.

Additionally, Scan2 (using MBPulse2) has higher peak RF power requirements compared to Scan1 (using MBPulse1), and may encounter problems if the peak RF requirement is too high.

Another type of mapping that is commonly employed in MR imaging is called B1 mapping. The B1 field is the RF field that is collectively produced in the examination object by the RF radiator. In the case of a non-uniform examination object such as a patient, different tissue and other objects such implants have respectively different magnetic susceptibilities and therefore differently affect the RF field within the patient. As a result, even though the RF radiator may be designed to emit a spatially uniform RF field, the RF field that actually occurs within the patient will have a non-uniform strength (magnitude) distribution. Techniques are known for making measurements that detect the different strengths of the RF field at a multitude of different spatial locations within the patient so that a map of this spatial distribution can then be calculated. This is known as B1 mapping. Such a B1 map has many uses in the context of MR imaging, such as correcting the resulting MR image, or making adjustments in the positions of the RF radiator and/or the patient prior to acquiring the diagnostic MR data.

SUMMARY OF THE INVENTION

An object of the present invention is to accelerate the raw data acquisition, such as for calculating T1 or B1 maps of multiple slices of an examination object, by using an SMS acquisition sequence, but wherein the aforementioned problems are avoided.

The above object is achieved in accordance with the invention in a magnetic resonance apparatus, and a method for operating the data acquisition scanner thereof, in order to acquire raw MR data with an SMS sequence wherein, in the SMS sequence, the MB RF pulse is generated from multiple SB RF pulses, which are simultaneously emitted and superimposed, with each SB RF pulse having a different flip angle. In other words, none of the SB RF pulses that are superimposed in order to form the MB RF pulse have the same flip angle.

In the above example with raw data being simultaneously acquired from two slices, an SMS acceleration factor of two, and two flip angles Flip1 and Flip2, with Flip2>Flip1, the scans executed in accordance with the invention would be:

Scan1: MBPulse1=SBPulse_Slice1_Flip1+
SBPulse_Slice2_Flip2

Scan2: MBPulse2=SBPulse_Slice1_Flip2+
SBPulse_Slice2_Flip1

In accordance with the invention, the two scans can have equal RF energy deposition, and thus present a lower likelihood, compared to the conventional sequence described earlier, that the SAR limit would be exceeded.

Moreover, the two scans can be executed with the same RF power requirements, thus presenting a lower likelihood than the conventional sequence of encountering peak RF power difficulties.

DESCRIPTION OF THE PREFERRED EMBODIMENTS

Figure 1:
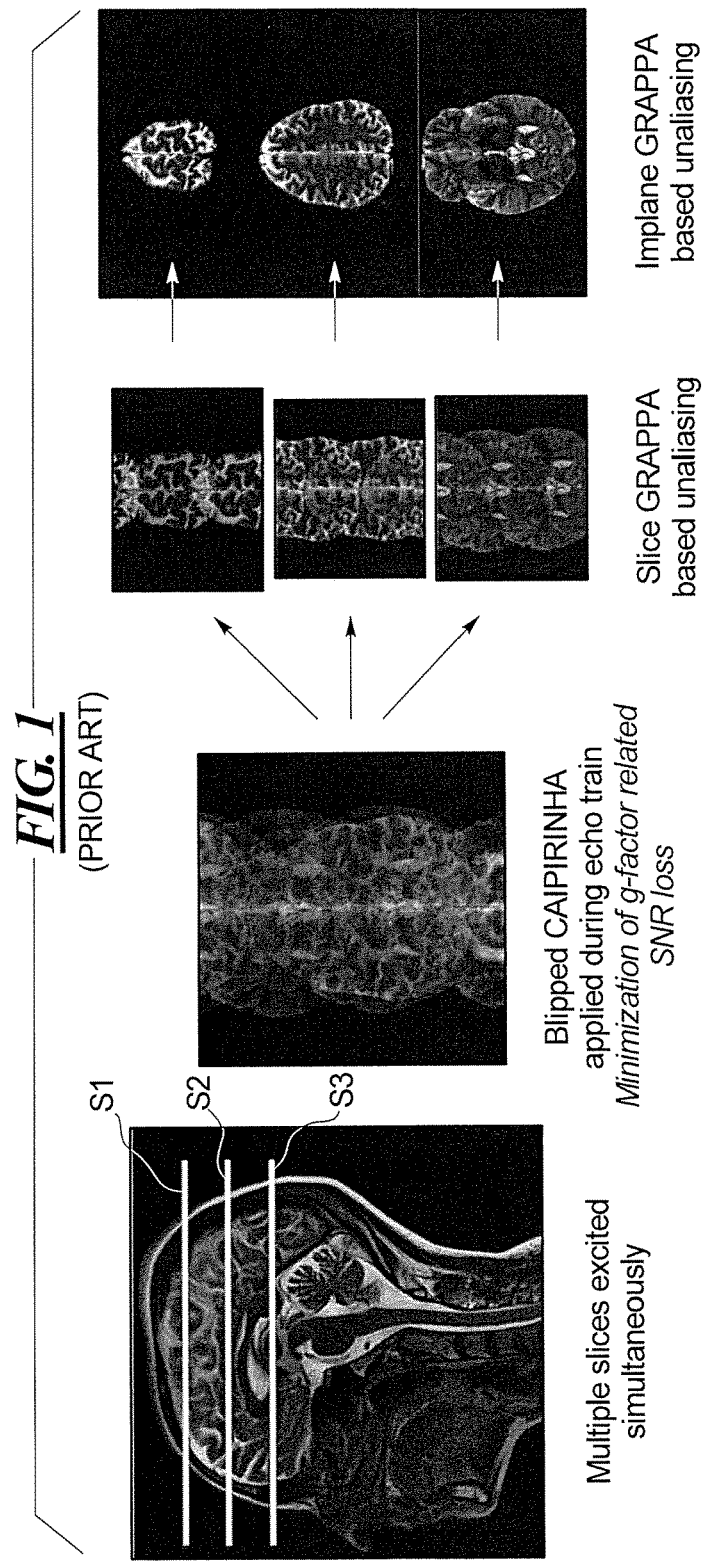
FIG. 1, as noted above, schematically illustrates a conventional SMS acceleration technique.
Figure 2:
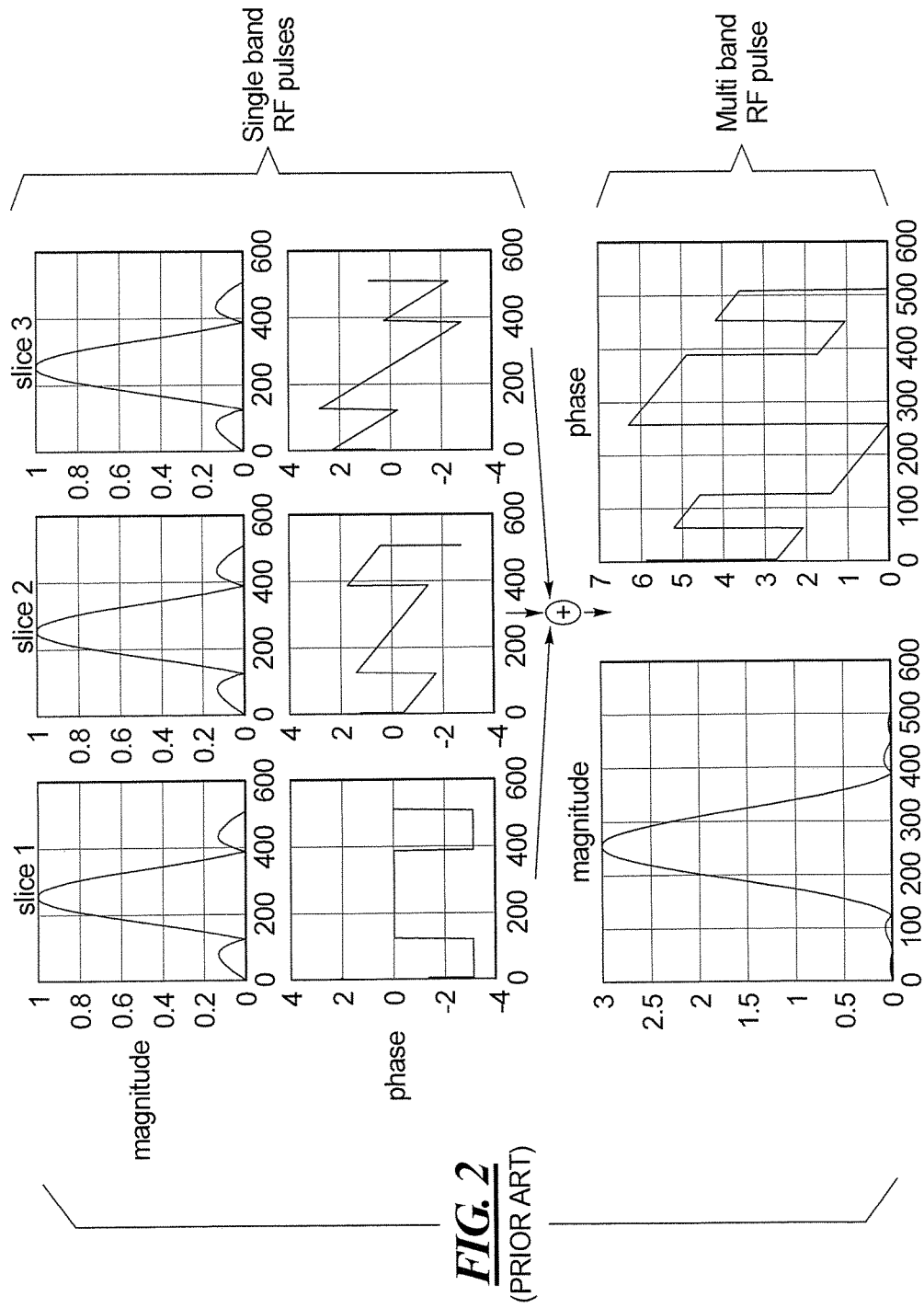
FIG. 2, as noted above, schematically illustrates the conventional generation of the MB RF pulse, from multiple SB RF pulses all having the same flip angle, in a conventional SMS sequence.
Figure 3:
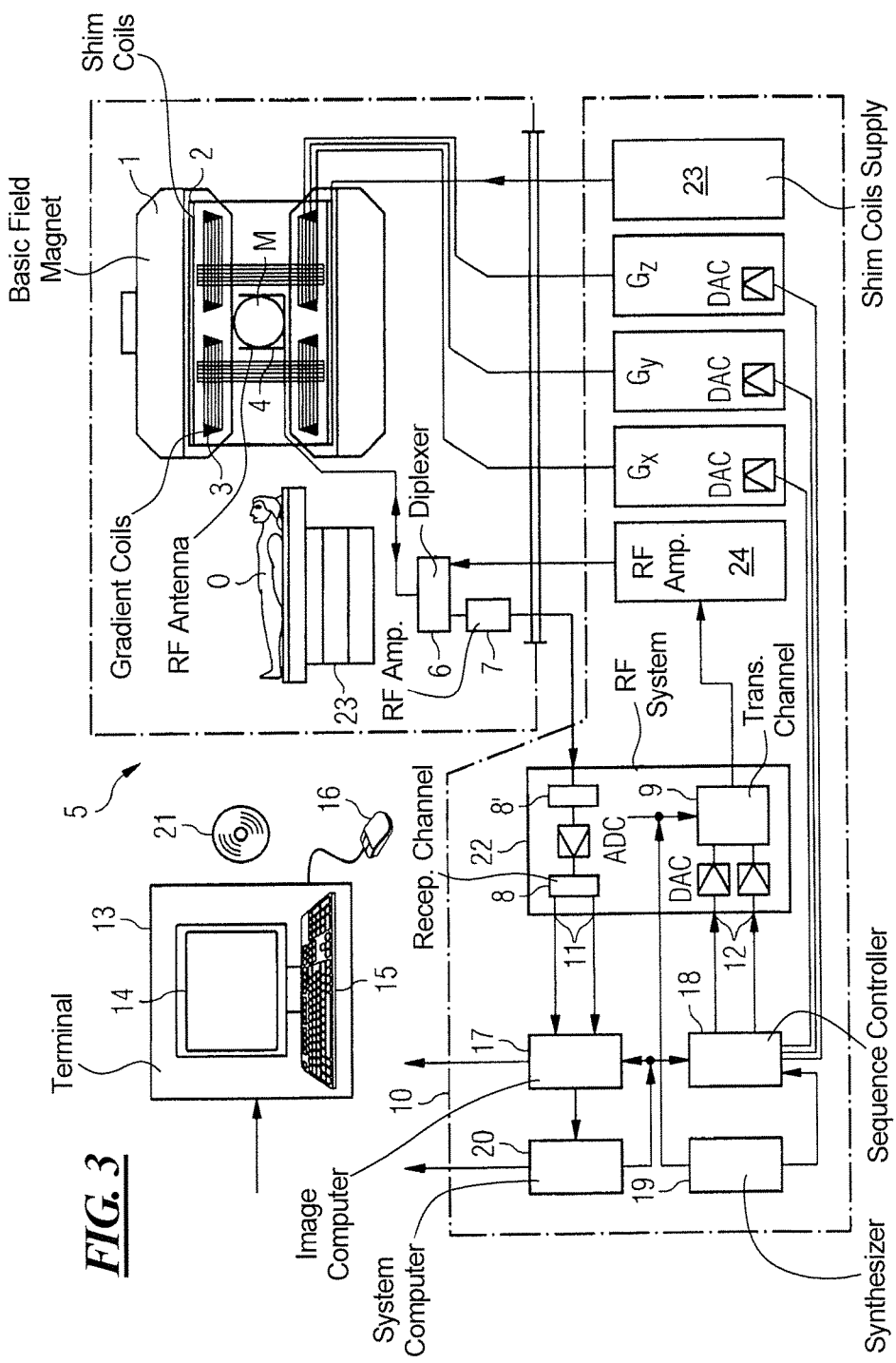
FIG. 3 schematically illustrates a magnetic resonance apparatus constructed and operating in accordance with the invention.

FIG. 3 schematically illustrates a magnetic resonance apparatus 5 (a magnetic resonance imaging or tomography device). A basic field magnet 1 generates, a temporally constant strong magnetic field for the polarization or alignment of the nuclear spin in a region of an examination subject O, such as a portion of a human body that is to be examined, lying on a table 23 in order to be moved into the magnetic resonance apparatus 5. The high degree of homogeneity in the basic magnetic field necessary for the magnetic resonance measurement (data acquisition) is defined in a typically sphere-shaped measurement volume M, in which the portion of the human body that is to be examined is placed. In order to support the homogeneity requirements temporally constant effects are eliminated by shim-plates made of ferromagnetic materials are placed at appropriate positions. Temporally variable effects are eliminated by shim-coils 2 and an appropriate control unit 27 for the shim-coils 2.

A cylindrically shaped gradient coil system 3 is incorporated in the basic field magnet 1, composed of three windings. Each winding is supplied by a corresponding amplifier 24-26 with power for generating a linear gradient field in a respective axis of a Cartesian coordinate system. The first partial winding of the gradient field system 3 generates a gradient $G_x$ in the x-axis, the second partial winding generates a gradient $G_y$ in the y-axis, and the third partial winding generates a gradient $G_z$ in the z-axis. Each amplifier 24-26 has a digital-analog converter (DAC), controlled by a sequencer 18 for the accurately-times generation of gradient pulses.

A radio-frequency antenna 4 is located within the gradient field system 3, which converts the radio-frequency pulses provided by a radio-frequency power amplifier into a magnetic alternating field for the excitation of the nuclei by tipping ("flipping") the spins in the subject or the region thereof to be examined, from the alignment produced by the basic magnetic field. The radio-frequency antenna 4 is composed of one or more RF transmitting coils and one or more RF receiving coils in the form of an annular, linear or matrix type configuration of coils. The alternating field based on the precessing nuclear spin, i.e. the nuclear spin echo signal normally produced from a pulse sequence composed of one or more radio-frequency pulses and one or more gradient pulses, is also converted by the RF receiving coils of the radio-frequency antenna 4 into a voltage (measurement signal), which is transmitted to a radio-frequency system 22 via an amplifier 7 of a radio-frequency receiver channel 8, 8'. The radio-frequency system 22 furthermore has a transmitting channel 9, in which the radio-frequency pulses for the excitation of the magnetic nuclear resonance are generated. For this purpose, the respective radio-frequency pulses are digitally depicted in the sequencer 18 as a series of complex numbers, based on a given pulse sequence provided by the system computer 20. This number series is sent via an input 12, in each case, as real and imaginary number components to a digital-analog converter (DAC) in the radio-frequency system 22 and from there to the transmitting channel 9. The pulse sequences are modulated in the transmitting channel 9 to a radio-frequency carrier signal, the base frequency of which corresponds to the resonance frequency of the nuclear spin in the measurement volume. The modulated pulse sequences of the RF transmitter coil are transmitted to the radio-frequency antenna 4 via an amplifier 28.

Switching from transmitting to receiving operation occurs via a transmission-receiving switch 6. The RF transmitting coil of the radio-frequency antenna 4 radiates the radio-frequency pulse for the excitation of the nuclear spin in the measurement volume M and scans the resulting echo signals via the RF receiving coils. The corresponding magnetic resonance signals obtained thereby are demodulated to an intermediate frequency in a phase sensitive manner in a first demodulator 8' of the receiving channel of the radio-frequency system 22, and digitalized in an analog-digital converter (ADC). This signal is then demodulated to the base frequency. The demodulation to the base frequency and the separation into real and imaginary parts occurs after digitization in the spatial domain in a second demodulator 8, which emits the demodulated data via outputs 11 to an image processor 17. In an image processor 17, an MR image is reconstructed from the measurement data obtained in this manner through the use of the method according to the invention, which includes computation of at least one disturbance matrix and the inversion thereof, in the image processor 17. The management of the measurement data, the image data, and the control program occurs via the system computer 20. The sequencer 18 controls the generation of the desired pulse sequences and the corresponding scanning of k-space with control programs, in particular, in accordance with the method according to the invention. The sequencer 18 controls accurately-timed switching (activation) of the gradients, the transmission of the radio-frequency pulse with a defined phase amplitude, and the reception of the magnetic resonance signals. The time base for the radio-frequency system 22 and the sequencer 18 is provided by a synthesizer 19. The selection of appropriate control programs for the generation of an MR image, which are stored, for example, on a DVD 21, as well as other user inputs such as a desired number n of adjacent clusters, which are to collectively cover the desired k-space, and the display of the generated MR images, occurs via a terminal 13, which includes units for enabling input entries, such as, e.g. a keyboard 15, and/or a mouse 16, and a unit for enabling a display, such as, e.g. a display screen.

The components within the dot-dash outline S are commonly called a magnetic resonance scanner.

Figure 4:
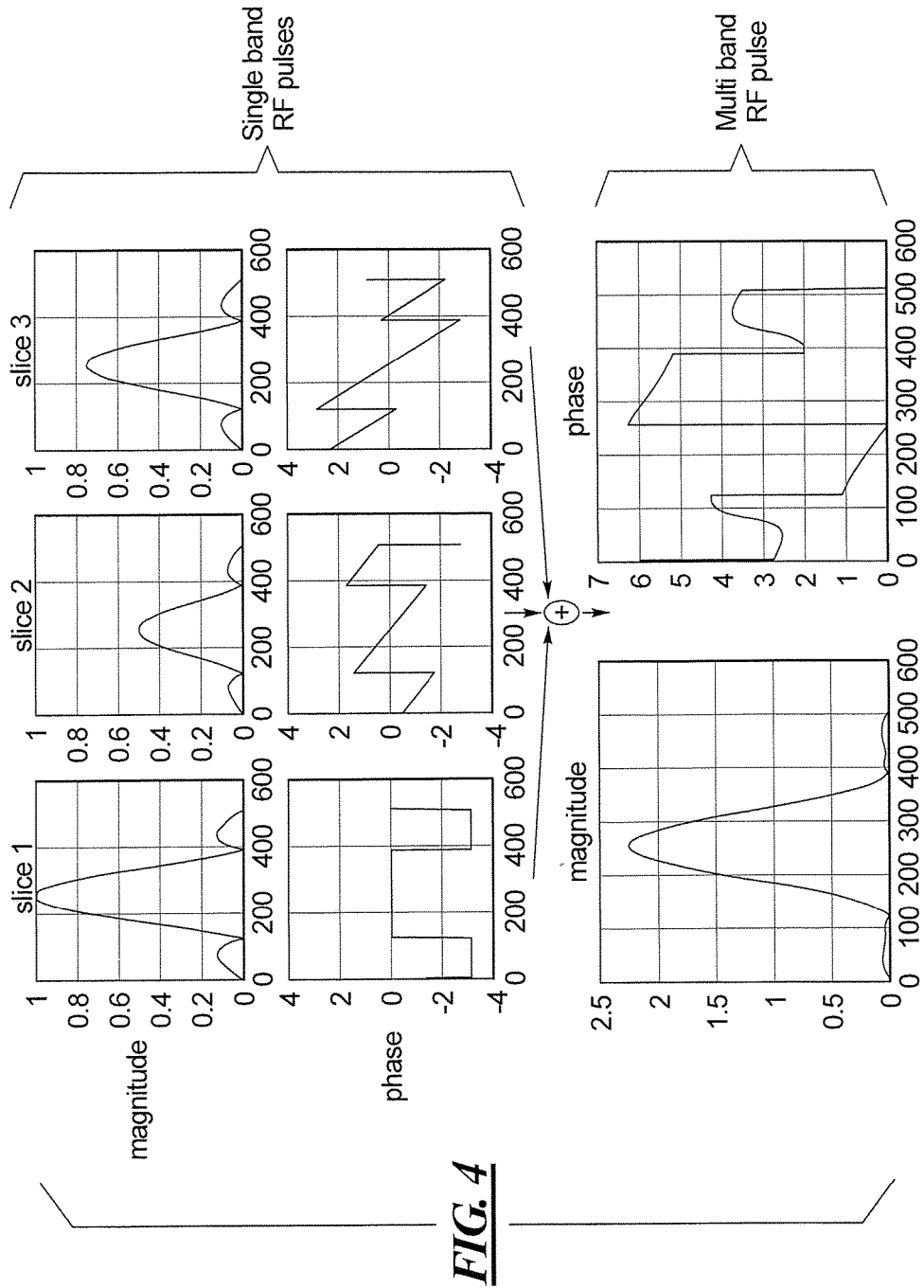
FIG. 4 schematically illustrates the generation of an MB RF pulse from multiple SB RF pulses having respectively different flip angles in the SMS sequence in accordance with the present invention.

As shown in FIG. 4, in the SMS sequence in accordance with the invention the MB RF pulse is produced from multiple SB RF pulses, having respectively different flip angles. As represented by the respective magnitudes for the respective SB RF pulses for, in this example, three slices (Slice 1, Slice 2 and Slice 3), each SB RF pulse has a flip angle that differs from each of the other SB RF pulses. These SB RF pulses with respectively different flip angles are simultaneously emitted by the RF radiator, which may be composed of multiple, individual coils, so as to be superimposed in the volume, formed by Slice1, Slice2 and Slice3, as the MB RF pulse that is shown at the bottom of FIG. 4. The simultaneous emission and superimposition of the individual SB RF pulses is schematically indicated in FIG. 4 by the summation element indicated with "+" in FIG. 4.

As discussed above, this results in the raw data for all of Slice 1, Slice 2 and Slice 3 being combined in the electronic memory that is organized as k-space, and, in order to reconstruct respective images of Slice 1, Slice 2 and Slice 3, the combined data must be separated. This can be done by a separation and image reconstruction algorithm of the type known for magnetic resonance images resulting from parallel, or partially parallel acquisition of the raw MR data. An example of such a data separation and image reconstruction algorithm suitable for this purpose is the aforementioned slice GRAPPA technique.

The reconstructed images can then be used to generate one or more T1 maps, also in a known manner.

The SMS sequence with the MB pulse produced from multiple SB pulses having respectively different flip angles can also be used to benefit in generating a B1 map. The SMS technique described herein would significantly accelerate the acquisition of the data needed to generate a B1 map, and using two different slip angles for two slices excited simultaneously will keep the SAR from being excessive, as might be the case if the same two slices were simultaneously excited with the same flip angle.

As also noted above, the raw data can be acquired in multiple successive scans wherein, in each of those successive scans, the RF excitation is produced by an MB RF pulse that is generated by the superimposition of multiple SB RF pulses with different flip angles, as shown in FIG. 4. A primary advantage of the invention is that, in such multiple scans, the use of SB RF pulses with respectively different flip angles allows improved adaptation in order to avoid exceeding SAR limits, as well as improving the ability to avoid problems associated with adherence to RF power requirements of the MR data acquisition scanner.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for acquiring magnetic resonance (MR) raw data, comprising:

operating an MR data acquisition scanner, while an examination subject is situated therein, to execute a plurality of successive MR data acquisition scans of the examination subject by, in each of said scans, executing a simultaneous multi-slice (SMS) data acquisition sequence in which nuclear spins respectively in multiple slices of the examination subject are simultaneously excited by radiating, from a radio-frequency (RF) radiator of said MR data acquisition scanner, a multi-band (MB) RF pulse into all of said multiple slices;

generating said MB RF pulse in each SMS data acquisition sequence in each scan by radiating and superimposing a plurality of single band (SB) RF pulses emitted from said RF radiator, each having a respectively different flip angle;

in the operation of the MR data acquisition scanner in each SMS data acquisition sequence in each scan, acquiring raw MR data from said multiple slices of the examination subject after said simultaneous excitation of nuclear spins in the multiple slices with said MB RF pulse so that the respective SB RF pulses that are superimposed in said MB RF pulse individually give said nuclear spins in the respective multiple slices said respectively different flip angles, and entering the acquired raw MR data from all of said multiple slices as k-space data into an electronic memory, organized as k-space;

in said successive scans, radiating the MB RF pulse therein so that the different flip angles of the SB RF pulses are applied to different ones of the multiple slices in different successive scans so as to reduce a peak RF power resulting from said MB RF pulse in the respective successive scans; and via a computer having access to said electronic memory, making the k-space data in said electronic memory available in electronic form, as a data file.

2. A method as claimed in claim 1 wherein the acquired raw MR data from said multiple slices represent signals emitted by the excited nuclear spins in said multiple slices, each signal having a signal intensity dependent on a T1 relaxation time of the nuclear spins, and comprising:

separating the respective k-space data for the respective multiple slices in k-space;

reconstructing an MR image for each slice among said multiple slices; and generating a T1 map for said multiple slices from the reconstructed MR images.

3. A method as claimed in claim 1 comprising separating said k-space data for the multiple slices in k-space, and reconstructing image data for each of said multiple slices, by executing a parallel reconstruction algorithm in said computer, and displaying the image data at a display screen in communication with said computer, as respective images of the multiple slices.

4. A method as claimed in claim 3 comprising using the slice Generalized Autocalibrating Partially Parallel Acquisitions (slice GRAPPA) reconstruction algorithm as said parallel acquisition reconstruction algorithm.

5. A method as claimed in claim 1 comprising acquiring said MR raw data by operating said MR data acquisition scanner to acquire said MR raw data in a plurality of successive scans, and generating the MB RF pulse in at least two of said successive scans with the different flip angles of the respective SB RF pulses being the same in said at least two of said successive scans.

6. A method as claimed in claim 1 wherein each of said SB RF pulses has a peak power, and comprising operating said MR data acquisition scanner to acquire said MR raw data in a plurality of successive scans, generating the MB RF pulse and, in at least two of said successive scans with the peak power of the SB RF pulses being the same.

7. A method as claimed in claim 1 comprising, in said computer, using the acquired raw MR data from said multiple slices of the examination subject to calculate a map of a spatial distribution of the strength of an RF field in the examination subject produced by said MB RF pulse, and making said map available in electronic form, as a data file, from said computer.

8. A magnetic resonance (MR) apparatus comprising:

an MR data acquisition scanner comprising a radiofrequency (RF) radiator;

a computer configured to operate said MR data acquisition scanner, while an examination subject is situated therein, to execute a plurality of successive MR data acquisition scans of the examination subject by, in each of said scans, executing a simultaneous multi-slice (SMS) data acquisition sequence in which nuclear spins respectively in multiple slices of the examination subject are simultaneously excited by radiating, from said RF radiator, a multi-band (MB) RF pulse into all of said multiple slices;

operating said RF radiator in each SMS data acquisition sequence in each scan to generate said MB RF pulse by radiating and superimposing a plurality of single band (SB) RF pulses emitted from said RF radiator, each having a respectively different flip angle;

an electronic memory organized as k-space;

said computer being configured to operate said MR data acquisition scanner in each SMS data acquisition sequence in each scan, to acquire raw MR data from said multiple slices of the examination subject after said simultaneous excitation of nuclear spins in the multiple slices with said MB RF pulse so that the respective SB RF pulses that are superimposed in said MB RF pulse individually give said nuclear spins in the respective multiple slices said respectively different flip angles, and to enter the acquired raw MR data from all of said multiple slices as k-space data into said electronic memory;

said computer being configured to operate said MR data acquisition scanner in said successive scans, by radiating the MB RF pulse therein so that the different flip angles of the SB RF pulses are applied to different ones of the multiple slices in different successive scans so as to reduce a peak RF power resulting from said MB RF pulse in the respective successive scans; and said computer being configured to make the k-space data in said electronic memory available in electronic form, as a data file.

9. An apparatus as claimed in claim 8 wherein the acquired raw MR data from said multiple slices represent signals emitted by the excited nuclear spins in said multiple slices, each signal having a signal intensity dependent on a T1 relaxation time of the nuclear spins, and wherein:

said computer is configured to separate the respective k-space data for the respective multiple slices in k-space;

said computer is configured to reconstruct an MR image for each slice among said multiple slices; and said computer is configured to generate a T1 map for said multiple slices from the reconstructed MR images.

10. An apparatus as claimed in claim 9 comprising a display screen in communication with said computer wherein said computer is configured to separate said k-space data for the multiple slices in k-space, and to reconstruct image data for each of said multiple slices, by executing a parallel reconstruction algorithm in said computer, and to display the image data at said display screen in communication with said computer, as respective images of the multiple slices.

11. An apparatus as claimed in claim 10 wherein said computer is configured to use the slice Generalized Autocalibrating Partially Parallel Acquisitions (slice GRAPPA) reconstruction algorithm as said parallel acquisition reconstruction algorithm.

12. An apparatus as claimed in claim 9 wherein said computer is configured to operate said MR data acquisition scanner to acquire said MR raw data in a plurality of successive scans, and to generate the MB RF pulse in at least two of said successive scans with the different flip angles of the respective SB RF pulses being the same in said at least two of said successive scans.

13. An apparatus as claimed in claim 9 wherein each of said SB RF pulses has a peak power, and wherein said computer is configured to operate said MR data acquisition scanner to acquire said MR raw data in a plurality of successive scans and wherein, in at least two of said successive scans, with the peak power of the SB RF pulses being the same.

14. An apparatus as claimed in claim 8 wherein said computer is configured to use the acquired raw MR data from said multiple slices of the examination subject to calculate a map of a spatial distribution of the strength of an RF field in the examination subject produced by said MB RF pulse, and to make said map available in electronic form, as a data file, from said computer.

* * * * *